United States Patent
Katsumata et al.

(10) Patent No.: US 8,658,392 B2
(45) Date of Patent: Feb. 25, 2014

(54) METHOD FOR EVALUATING TOXICITY OF CHEMICAL USING ALGA

(75) Inventors: Masakazu Katsumata, Hamamatsu (JP); Ayano Takeuchi, Hamamatsu (JP); Kimiko Kazumura, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 13/508,436

(22) PCT Filed: Oct. 26, 2010

(86) PCT No.: PCT/JP2010/068986
§ 371 (c)(1),
(2), (4) Date: May 7, 2012

(87) PCT Pub. No.: WO2011/055658
PCT Pub. Date: May 12, 2011

(65) Prior Publication Data
US 2012/0231491 A1 Sep. 13, 2012

(30) Foreign Application Priority Data
Nov. 9, 2009 (JP) ................................. 2009-256172

(51) Int. Cl.
*C12Q 1/04* (2006.01)

(52) U.S. Cl.
USPC .......................................................... 435/34

(58) Field of Classification Search
USPC .................................................... 435/32, 34
See application file for complete search history.

(56) References Cited

U.S. PATENT DOCUMENTS

2007/0224659 A1* 9/2007 Katsumata et al. ............. 435/34

FOREIGN PATENT DOCUMENTS

| JP | 2008-116401 | | 5/2008 |
|----|----|----|----|
| JP | 2008-253150 | A | 10/2008 |
| WO | 2005/062027 | | 7/2005 |

OTHER PUBLICATIONS

Kuwano K. Morui no Toketsu Hozon. 21 Seiki Shoto no Mogaku no Genkyo. The Japanese Society of Phycology. 2002;108-111.*

F. Mori, et al., "Cryopreservation of Cyanobacteria and Green Algae in the NIES-Collection", Jun. 2002, Microbiol. Cult. Coll., vol. 18, No. 1, p. 45-55.

K. Kuwano, "Cryopreservation of Algae," Current State of Phycology in Early 21st Century, Japanese Society of Phycology, 2002, pp. 108-111, with English-language translation.

Supplementary European Search Report dated May 7, 2013 issued in European Appln. No. 10 82 8218.7.

S. Paixão et al., "Performance of a miniaturized algal bioassay in phytotoxicity screening," Ecotoxicology, Kluwer Academic Publishers, BO, vol. 17, No. 3, Nov. 4, 2007, pp. 164-171, XP019572029.

* cited by examiner

*Primary Examiner* — Ruth Davis
*Assistant Examiner* — Lynn Y Fan
(74) *Attorney, Agent, or Firm* — Drinker Biddle & Reath LLP

(57) ABSTRACT

The present invention provides a method for evaluating the toxicity of a chemical by using an alga, comprising: (a) a thawing step of thawing frozen algal cells by heating, and diluting the obtained suspension of the cells by adding a culture medium thereto; (b) a recovery culture step of culturing the algal cells obtained in the thawing step (a) to allow the algal cells to recover from the effects of freezing and thawing; (c) a confirmation step of collecting a part of the algal cells after the recovery culture step (b), diluting the part of the algal cells by adding a culture medium thereto, and measuring the amount of the luminescence of the delayed luminescence of the algal cells as initial value data; (d) an exposure step of mixing the algal cells after the confirmation step (c) with a solution containing a test substance to prepare an exposure sample, and culturing the exposure sample; (e) a measurement step of measuring the amount of the luminescence of the delayed luminescence of the exposure sample after the exposure step (d) as exposure data; and (f) an evaluation step of calculating an evaluation value based on the initial value data and the exposure data, and evaluating the toxicity of the test substance based on the evaluation value.

4 Claims, 8 Drawing Sheets

METHOD FOR EVALUATING TOXICITY OF CHEMICAL USING ALGA

TECHNICAL FIELD

The present invention relates to a method for evaluating a toxicity of a chemical by using an alga.

BACKGROUND ART

When the toxicity of a chemical is evaluated by using an alga, it is necessary to prepare algal cells by carrying out a primary culture and a successive culture of cells maintained in a liquid culture or on an agar culture medium, and then to carry out the test by adding the test substance to the prepared algal cells. However, it is troublesome and inconvenient to maintain algal cells and to carry out the successive culture for each test.

To resolve this troublesomeness, it is possible to use frozen algal cells (Non Patent Literatures 1 and 2, for example). By thawing the frozen algal cells immediately before the test and using the thawed algal cells, it is possible to rapidly provide the algal cells for the test without carrying out the successive culture of the algal cells.

CITATION LIST

Patent Literature
Patent Literature 1: International Publication No. WO 2005/062027
Non Patent Literature
Non Patent Literature 1: Kazuyoshi KUWANO, 2002, "Cryopreservation of Algae" in "Current State of Phycology in Early 21st Century" (Ed. Teruzo HORI, Masao OHNO, Takeo HORIGUCHI) Japanese Society of Phycology, Yamagata, pp. 108-111
Non Patent Literature 2: Fumi MORI et al., "Cryopreservation of cyanobacteria and green algae in the Microbial Culture Collection at the National Institute for Environmental Studies" Microbiol. Cult. Coll., June 2002, pp. 45-55

SUMMARY OF INVENTION

Technical Problem

The present inventors have already developed a method for evaluating the toxicity of a chemical by using an alga, utilizing delayed luminescence in an alga (Patent Literature 1), which is rapid and simple in comparison with the growth inhibition test described in the Organization for Economic Co-operation and Development (OECD) Test Guidelines TG201. However, the present inventors found that when the delayed luminescence was measured immediately after the thawing of frozen cells, the luminescence pattern was different from the delayed luminescence of the unfrozen cells, and also the amount of luminescence decreased. Accordingly, when frozen algal cells are used, disadvantageously, the toxicity evaluation equal to the evaluation using unfrozen algal cells cannot be achieved.

Solution to Problem

The present inventors studied hard to solve this problem, and have found that when the frozen algal cells are thawed, and then recovery culture is performed in which the algal cells is cultured to allow the cells to recover from the effect of freezing, the luminescence pattern obtained is the same as that of the unfrozen algal cells without reduction in an amount of the luminescence, and thus the present invention was completed.

That is, the present invention provides a method for evaluating the toxicity of a chemical by using an alga, comprising:

(a) a thawing step of thawing frozen algal cells by heating, and diluting the obtained suspension of the cells by adding a culture medium thereto;

(b) a recovery culture step of culturing the algal cells obtained in the thawing step (a) to allow the algal cells to recover from the effects of freezing and thawing;

(c) a confirmation step of collecting a part of the algal cells after the recovery culture step (b), diluting the part of the algal cells by adding a culture medium thereto, and measuring the amount of the luminescence of the delayed luminescence of the algal cells as initial value data;

(d) an exposure step of mixing the algal cells after the confirmation step (c) with a solution containing a test substance to prepare an exposure sample, and culturing the exposure sample;

(e) a measurement step of measuring the amount of the luminescence of the delayed luminescence of the exposure sample after the exposure step (d) as exposure data; and (f) an evaluation step of calculating an evaluation value based on the initial value data and the exposure data, and evaluating the toxicity of the test substance based on the evaluation value.

To carry out more accurate evaluation in the above method, the recovery culture step (b) and the confirmation step (c) are preferably repeated until the initial value data obtained in the confirmation step (c) reaches a predetermined value.

Also, to carry out more accurate evaluation in the above method, preferably, in the exposure step (d), the algal cells after the confirmation step (c) is also mixed with a solvent for the test substance solution to prepare a control sample, and the control sample is cultured; in the measurement step (e), the delayed luminescence of the control sample is also measured as control data; and in the evaluation step (f), an evaluation value is calculated based on the initial value data, the exposure data and the control data, and the toxicity of the test substance is evaluated based on the evaluation value.

Advantageous Effects of Invention

The method of the invention for evaluating a toxicity of a chemical by using an alga enables rapid evaluation of the toxicity by using frozen algal cells.

DESCRIPTION OF EMBODIMENTS

Hereinafter, the embodiments to practice the present invention are described in detail referring to the attached drawings.

Figure 8:
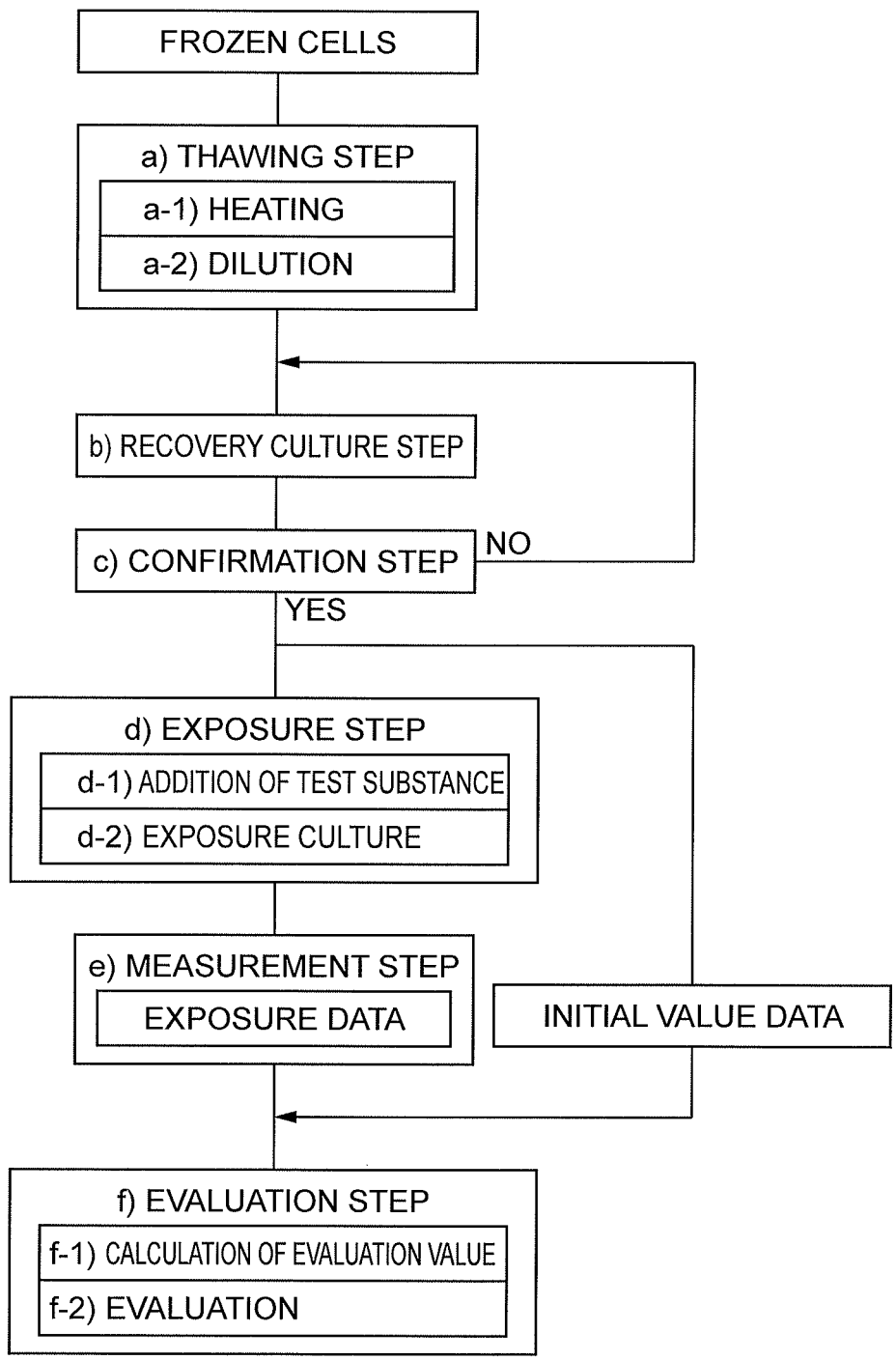
FIG. 8 is a flow chart illustrating the method for evaluating a toxicity of a chemical by using an alga according to Example.

FIG. 8 is a flow chart to explain the method for evaluating a toxicity of a chemical using an alga according to the embodiment. The embodiment includes a thawing step (a), a recovery culture step (b), a confirmation step (c), an exposure step (d), a measurement step (e) and an evaluation step (f).

In the thawing step (a), the frozen algal cells are thawed by heating, and a suspension of the cells obtained by thawing is diluted by adding a culture medium thereto.

The frozen algal cells to be used may be algal cells frozen by an ordinary freezing method for algal cells. Thawing can be carried out, for example, by slowly shaking the cryotube containing frozen cells in a water bath of 37° C. for about 120-150 seconds.

Next, the suspension of the thawed cells is diluted by adding a culture medium thereto. The frozen cell suspension usually contains a freezing damage protectant such as dimethylsulfoxide (DMSO), and in order to alleviate the cell toxicity of the freezing damage protectant, it is necessary to dilute the suspension as soon as possible after thawing. The dilution may be, for example, a ten-fold dilution using an OECD culture medium. To prevent drastic change in osmolarity, the culture medium is added slowly over about 1 minute.

In the recovery culture step (b), the algal cells obtained in the thawing step (a) are cultured to allow the algal cells to recover from the effects of the freezing and thawing. As shown in Comparative Example described later, without the recovery culture step, the algal cells cannot recover from the damage of the freezing and thawing sufficiently, the luminescence pattern of the delayed luminescence will change and the amount of luminescence will lower in comparison with the unfrozen algal cells. Unless the frozen and thawed algal cells show the same luminescence pattern and luminescence amount as the unfrozen algal cells do, an appropriate evaluation of the toxicity of the chemical cannot be achieved. As shown in the following Example, when the recovery culture step (b) is carried out after the thawing step (a), the frozen and thawed algal cells become to show the same luminescence pattern and the same luminescence amount as the unfrozen algal cells to enable to solve the problem. In the recovery culture, the culturing is performed, for example, for 1-2 hours under the conditions of a temperature of 25±0.5° C., and an illuminance of 50-55 $\mu mol \cdot m^{-2} \cdot s^{-1}$.

In the confirmation step (c), a part of the algal cells after the recovery culture step (b) is collected and diluted by adding a culture medium thereto, the delayed luminescence of the algal cells is measured, and the measured amount of the luminescence is defined as initial value data. In this step, sufficient recovery of the algal cells from the effect of the freezing and thawing by the recovery culture step (b) is confirmed, and the initial value data is obtained to be used in the later toxicity evaluation.

The reason why the algal cells are further diluted with the culture medium is to alleviate the toxicity of the freezing damage protectant. Usually, the freezing damage protectant is contained in the frozen cell suspension in a concentration of about 5-10%. When about 10-fold dilution is carried out in the thawing step (a), the concentration of the freezing damage protectant becomes around 0.5-1%, and it has been found that the recovery step is possible under such a concentration of the freezing damage protectant. However, in order not to affect the toxicity evaluation of a chemical, it is necessary to carry out further 10-fold dilution after the culture to reduce the concentration of the freezing damage protectant.

Measurement of delayed luminescence can be carried out by using the known apparatus and method, for example, those described in International Publication No. WO2005/062027.

When the luminescence amount measured in the confirmation step (c) is the predetermined value, using the value as the initial value data, one can progress to the next exposure step (d). As the predetermined value to be the criterion, a previously set value or an individually set value for frozen cells may be used. For example, the manufacturer can set the value at the production of the frozen cells. The predetermined value is, for example, a value of 90% or more of the luminescence amount of the unfrozen algal cells. With a value smaller than this value, the luminescence amount is insufficient, and the recovery of the algal cells is judged to be insufficient.

When the luminescence amount measured in the confirmation step (c) does not reach the predetermined value, the recovery culture step (b) is continued, and after a certain period of time, e.g., 30 minutes, the confirmation step is carried out again to confirm whether the value has reached the predetermined value or not.

In the exposure step (d), algal cells whose recovery from the effect of the freezing and thawing has been sufficiently confirmed by the confirmation step (c) are mixed with a solution containing the test substance to prepare the exposure sample, and the exposure sample is cultured.

Preparation of the exposure sample is as follows: for example, to 1 volume of algal cells, 9 volumes of a solution containing the test substance is added. By this operation, the algal cells are diluted 10-fold, which is, as described above, to avoid the effect of the freezing damage protectant onto the toxicity evaluation of the chemical. This operation also enables addition of a large amount of a solution containing the test substance, which enables evaluation of a chemical that is hardly soluble in water. Plural exposure samples may be prepared by varying the concentration of the test substance. Also a control sample may be prepared by mixing the algal cells and the solvent used to dissolve the test substance alone. Evaluation of the toxicity of the test substance can be carried out more accurately by measuring the control data using the control sample, and then calculating the evaluation value.

Culturing of the exposure sample is carried out, for example, under the conditions of a temperature of 25±0.5° C. and an illuminance of 50-55 $\mu mol \cdot m^{-2} \cdot s^{-1}$. Culture period is not specifically limited as long as it allows the test substance to exert influence on the algal cells, but, for example, it is 8 hours, preferably 24 hours. To make the measurement of the delayed luminescence easier, the vessel for culturing of the exposure sample may be a test tube that can be used directly in the measurement of the delayed luminescence. In that case, to minimize variation in illuminance between the test tubes, to increase agitation efficiency, and to increase the algal cell growth rate, it is preferable to carry out rotation culture using a rotator and an orbital shaker in combination.

In the measurement step (e), the delayed luminescence of the exposure sample after the exposure step (d) is measured, and the measured amount of the luminescence is defined as exposure data. As described above, measurement of the delayed luminescence can be carried out by the known method and apparatus, for example, the method and apparatus disclosed in International Publication No. WO2005/062027. More specifically, the sample was irradiated with excitation light (680 nm, 20 μmol·m$^{-2}$·s$^{-1}$) for 1 second, then the delayed luminescence detected from the sample is detected by using a photomultiplier, the amount of the delayed luminescence is recorded after the completion of excitation for 60 seconds at an interval of 100 milliseconds, and the total of the delayed luminescence amounts from 1.1 seconds to 60 seconds after the completion of excitation is defined as the exposure data.

In the evaluation step (f), an evaluation value is calculated based on the initial value data and the exposure data, and the toxicity of the test substance is evaluated based on the evaluation value. The luminescence amount of the delayed luminescence is known to decrease in correlation with the growth inhibition of algal cells. When the luminescence amount of the exposure data is lower than that of the initial value data, the test substance can be evaluated as having toxicity. More specifically, measurement is carried out with exposure samples, one containing a harmful substance to be evaluated (sample A), and one not containing the harmful substance (sample B), and the increase rate for each is calculated according to the following equation (1), to compare the increase rates of A and B, and the decreased amount of A to B is calculated according to the following equation (2) as an index of toxicity.

$$\text{Increase rate}=(\ln(\text{exposure data})-\ln(\text{initial value data}))\div(\text{culture period}) \quad \text{Equation (1)}$$

$$\text{Decrease rate}=(\text{increase rate of } B-\text{increase rate of } A)\div(\text{increase rate of } B)\times 100 \quad \text{Equation (2)}$$

EXAMPLES

Comparative Example

Green alga (*Pseudokirchneriella subcapitata*) frozen according to standard procedures under the following conditions of: in a volume of 650 μl, a cell density of 2000×10$^4$ cells/ml, in the presence of freezing damage protectant (5% DMSO); was used to measure delayed luminescence according to the following process. As the dilution solution, an OECD culture medium was used.

(a) Thawing Step
(a-1) Heating Step

A cryotube containing the frozen green alga was slowly shaken in a water bath at 37° C. for about 120-150 seconds and completely thawed. In a clean bench, the thawed green alga was lightly pipetted using a pipette having a large tip diameter and 620 μl of the cell suspension was transferred into a glass tube.

(a-2) Dilution Step

5580 μl of OECD culture medium (10-fold dilution) was slowly added into the glass tube. To avoid drastic change in osmolarity, the culture medium was added little by little over about 1 minute. After the addition of the culture medium, the tube was left standing in the bench for about 5-10 minutes.

(c) Confirmation Step

A part of the sample to which the dilution step (a-2) had been completed was collected and diluted 10-fold to prepare the initial value sample. The delayed luminescence of the initial value sample was measured. The cell number was also measured by particle counting. Further, viable cells were counted by a colony method. Meanwhile, using the unfrozen green alga, measurement of the delayed luminescence, particle counting and colony survival rate counting were carried out.

Figure 1:
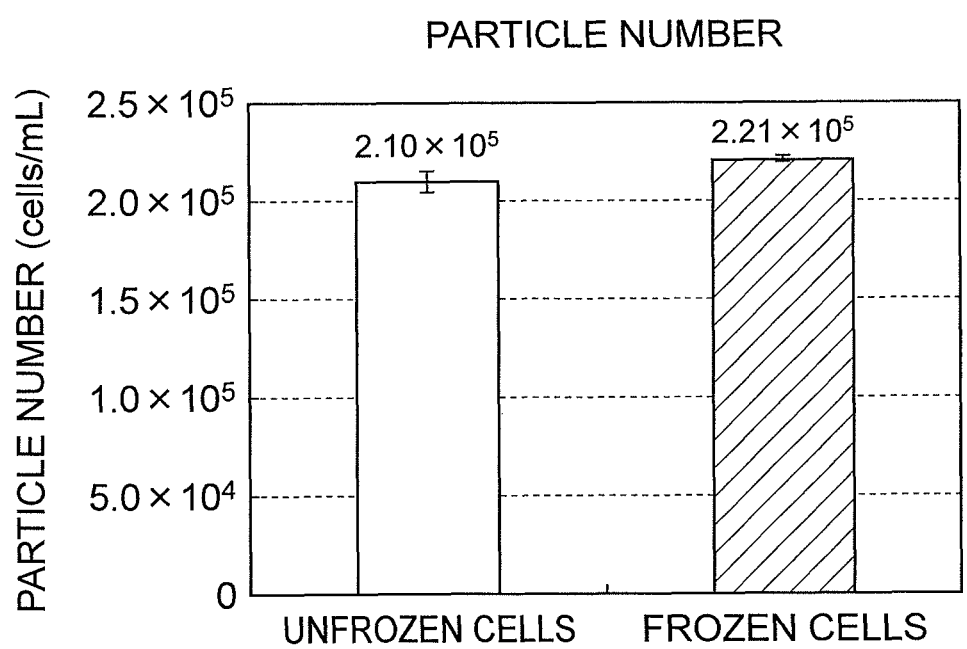
FIG. 1 is a graph showing particle numbers of the frozen and thawed green alga (Comparative Example) and the unfrozen green alga.
Figure 2:
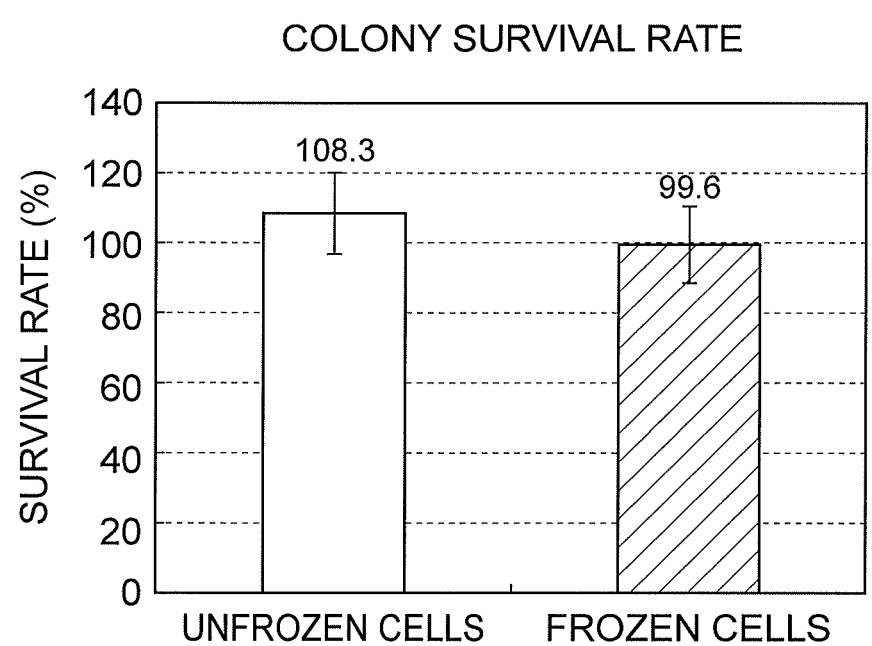
FIG. 2 is a graph showing colony survival rates of the frozen and thawed green alga (Comparative Example) and the unfrozen green alga.

FIG. 1 is a graph showing the particle number of the frozen and thawed green alga and that of the unfrozen green alga, and FIG. 2 is a graph showing the colony survival rate of the frozen and thawed green alga and that of the unfrozen green alga. It is clear from FIGS. 1 and 2 that the particle number and colony survival rate of the frozen and thawed green alga in the confirmation step (c) are rarely different from those of unfrozen green alga, so that the frozen and thawed green alga apparently recovered from the effect of the freezing and thawing to appropriate conditions.

Figure 3:
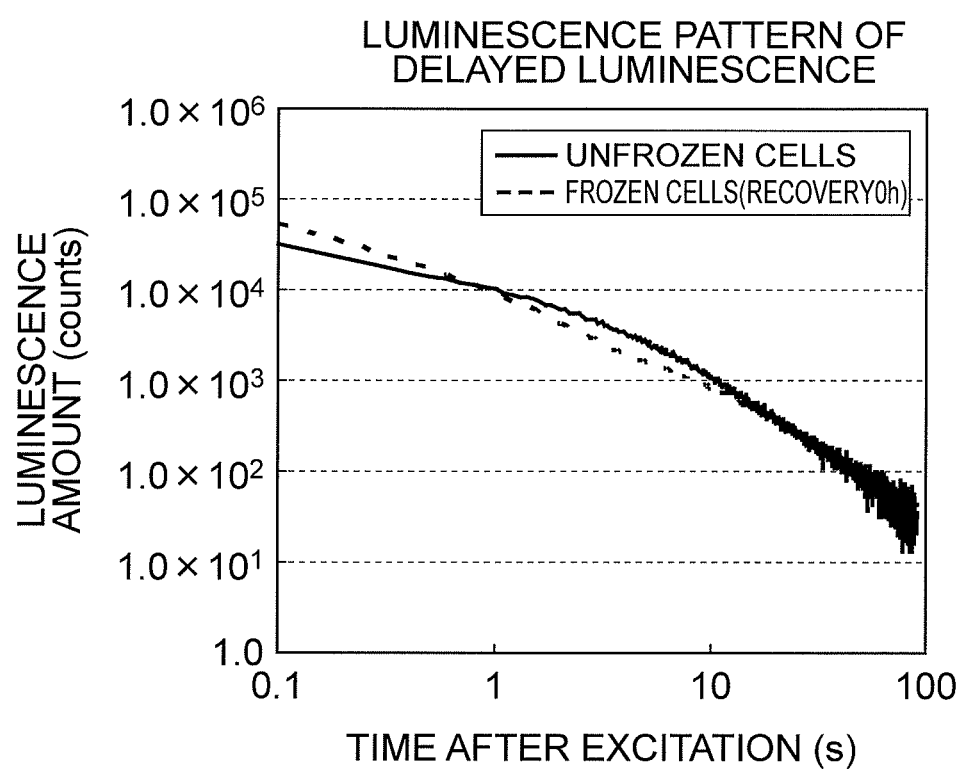
FIG. 3 is a graph showing luminescence patterns of the delayed luminescence of the frozen and thawed green alga (Comparative Example) and the unfrozen green alga.
Figure 4:
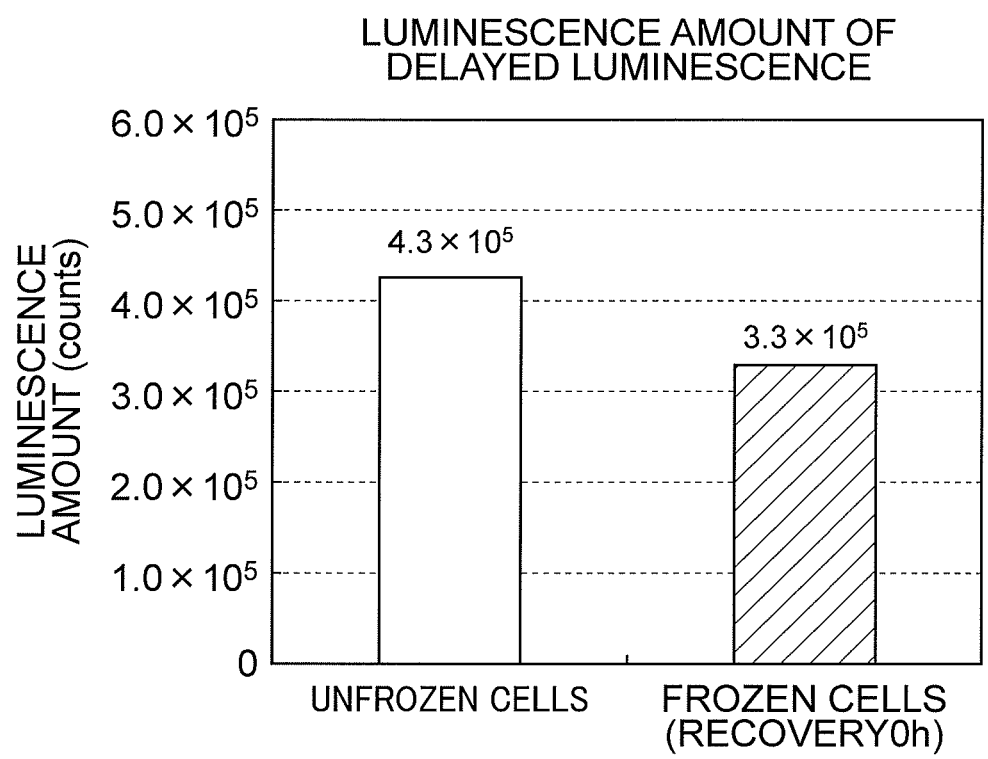
FIG. 4 is a graph showing the luminescence amounts (integrated value) of the frozen and thawed green alga (Comparative Example) and the unfrozen green alga.

However, from FIG. 3 that shows the luminescence patterns of delayed luminescence, it is seen that the frozen and thawed green alga and the unfrozen green alga are different in the luminescence pattern. If the luminescence patterns are different, an evaluation equivalent to the evaluation using the unfrozen alga cannot be made in the later toxicity evaluation of a chemical. FIG. 4 is a graph showing the luminescence amount (integrated value) from 1.1 seconds to 60 seconds after the excitation light was switched off, in which the luminescence amount of the frozen green alga is lower than that of the unfrozen green alga, i.e., approximately 77%. Delayed luminescence is known to decrease in correlation with the growth inhibition of alga. And thus, it is predicted that the growth inhibition has already occurred in the algal cells whose luminescence amount is lower than before freezing because of the freezing and thawing, and the toxicity cannot be evaluated properly when the cells are exposed to a subject chemical.

Accordingly, the method of above Comparative Example is not suitable for the method for evaluating a chemical by using delayed luminescence of an alga.

Example (a) A Thawing Step was Carried Out by the Same Method as in Comparative Example.

(b) Recovery Culture Step

The sample prepared in the thawing step (a) was cultured at a temperature of 25±0.5° C. and an illuminance of 50-55 μmol·m$^{-2}$·s$^{-1}$ for 1 or 2 hours.

(c) Confirmation Step

A part of the sample that had completed the recovery culture step (b) was collected and diluted to prepare the initial value sample. The delayed luminescence of the initial value sample was measured. Meanwhile, using an unfrozen green alga, measurement of the delayed luminescence was carried out.

Figure 5:
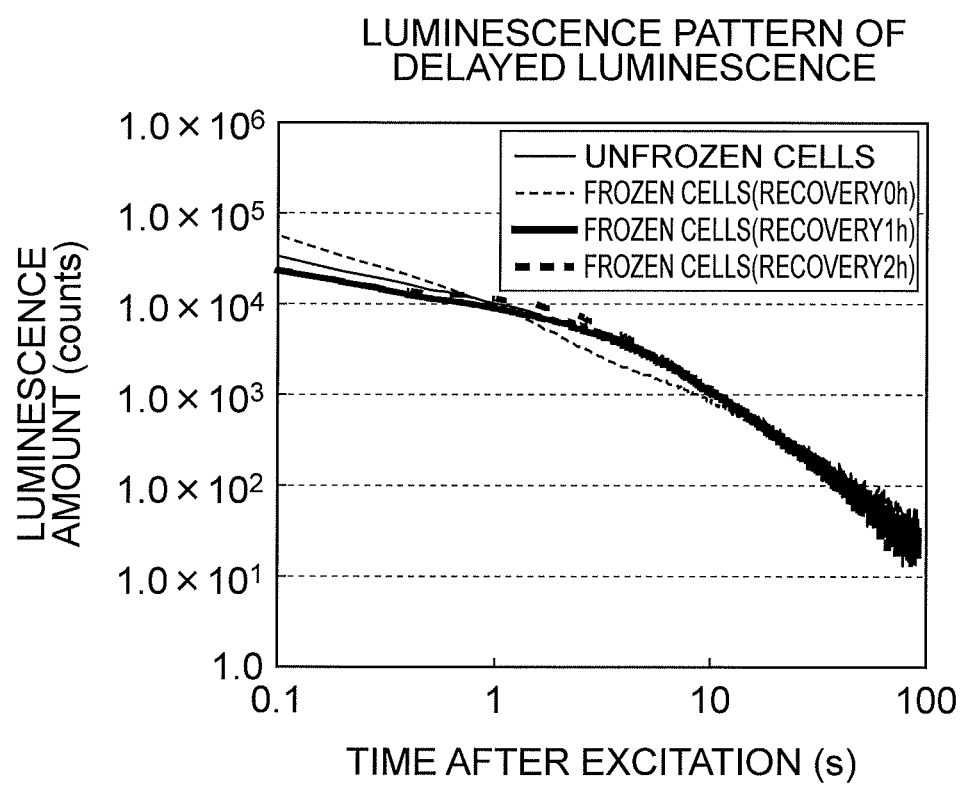
FIG. 5 is a graph showing luminescence patterns of the delayed luminescence of the frozen and thawed green alga (Example) and the unfrozen green alga.
Figure 6:
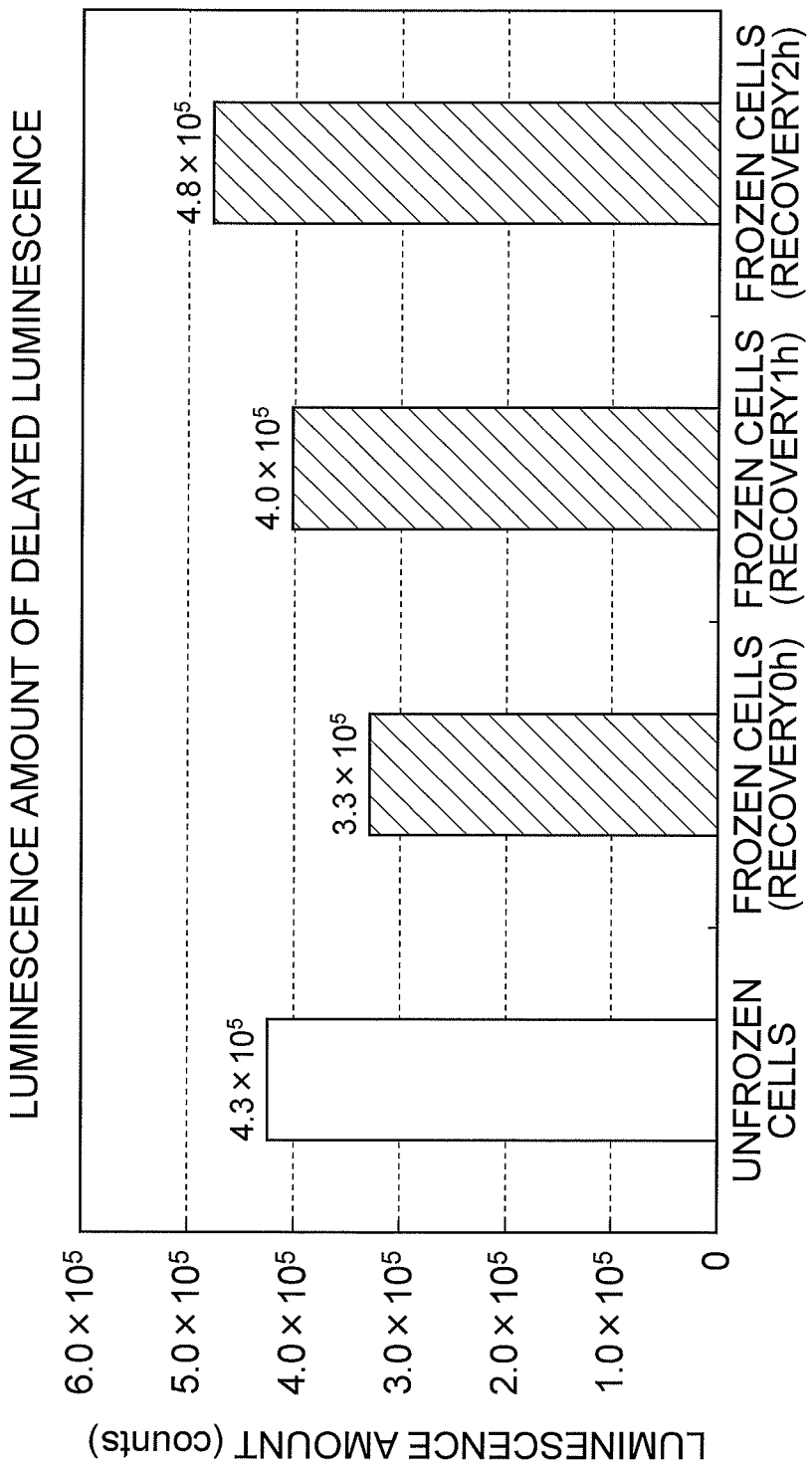
FIG. 6 is a graph showing the luminescence amounts (integrated value) of the frozen and thawed green alga (Example) and the unfrozen green alga.
Figure 7:
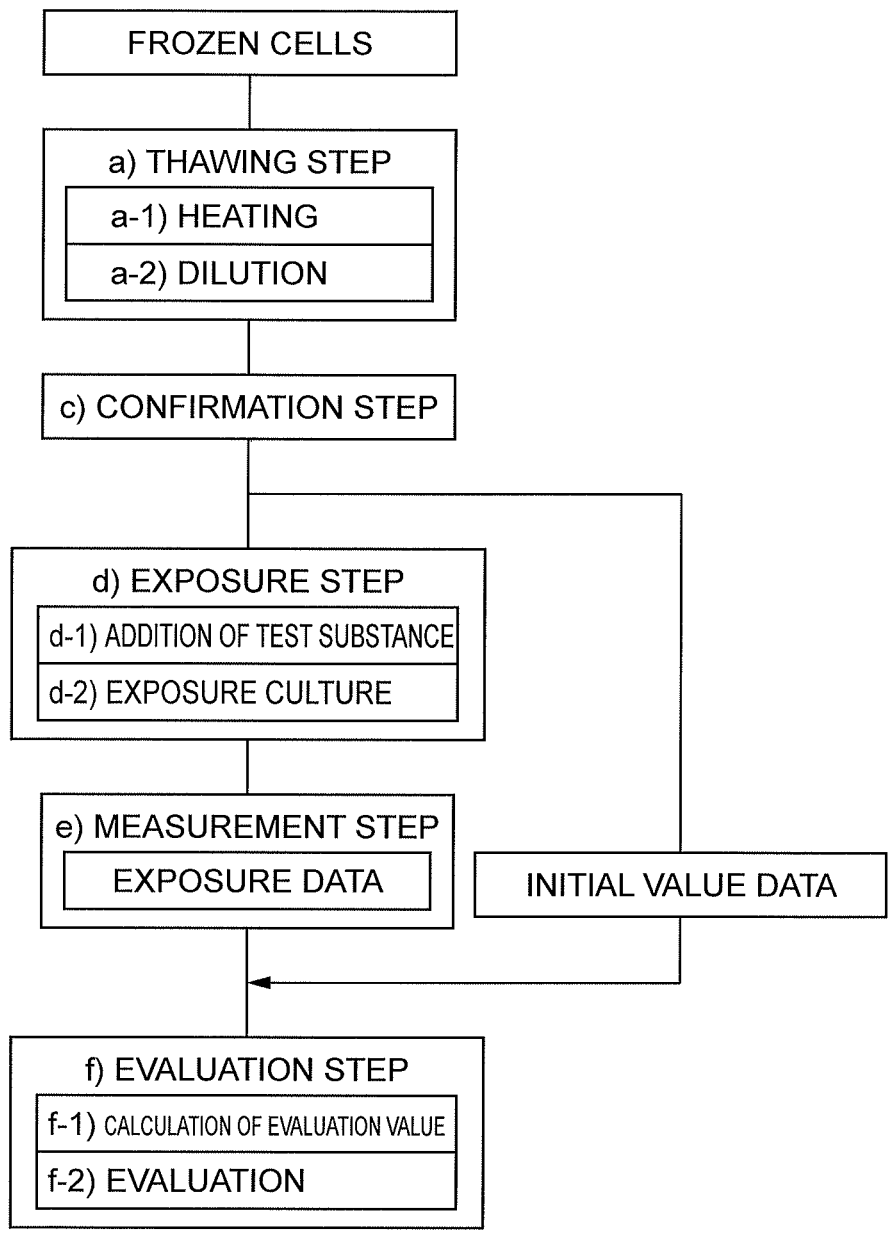
FIG. 7 is a flow chart illustrating the method for evaluating a toxicity of a chemical by using an alga according to Comparative Example.

FIG. 5 is a graph showing the luminescence pattern of the delayed luminescence. For comparison, there are included, in addition to the delayed luminescence of the unfrozen green alga and that of the initial value sample obtained by the method of Example, the delayed luminescence of the initial value sample obtained by the method of Comparative Example. It is clear from FIG. 5 that, by carrying out the recovery culture for 1 or 2 hours, the same luminescence pattern as with the unfrozen green alga was obtained. FIG. 6 is a graph showing the luminescence amount. By carrying out the recovery culture for 1 or 2 hours, the luminescence amounts respectively reached about 93% and about 112% of the luminescence amount of the unfrozen green alga, so that sufficient luminescence amounts were obtained. Thus the method of Example described above enables an evaluation equal to when unfrozen green alga is used.

The invention claimed is:

1. A method for evaluating the toxicity of a chemical by using an alga, comprising:
   (a) a thawing step of thawing frozen algal cells by heating, and diluting the obtained suspension of the cells by adding a culture medium thereto;
   (b) a recovery culture step of culturing the algal cells obtained in the thawing step (a) for about 1-2 hours at about 25° C. and at an illuminance of 50-55 $\mu mol \cdot m^{-2} \cdot s^{-1}$ to allow the algal cells to recover from the effects of freezing and thawing;
   (c) a confirmation step of collecting a part of the algal cells immediately after the recovery culture step (b), diluting the part of the algal cells by adding a culture medium thereto, and measuring the amount of the luminescence of the delayed luminescence of the algal cells as initial value data;
   (d) an exposure step of mixing the algal cells after the confirmation step (c) with a solution containing a test substance to prepare an exposure sample, and culturing the exposure sample;
   (e) a measurement step of measuring the amount of the luminescence of the delayed luminescence of the exposure sample after the exposure step (d) as exposure data; and
   (f) an evaluation step of calculating an evaluation value based on the initial value data and the exposure data, and evaluating the toxicity of the test substance based on the evaluation value, wherein the test substance is evaluated as having toxicity if the exposure data is lower than the initial value data.

2. The method according to claim 1, wherein the recovery culture step (b) and (c) are repeated until the initial value data obtained in the confirmation step (c) reaches a predetermined value.

3. The method according to claim 1, wherein
   in the exposure step (d), the algal cells after the confirmation step (c) is also mixed with a solvent for the test substance solution to prepare a control sample, and the control sample is cultured;
   in the measurement step (e), the delayed luminescence of the control sample is also measured as control data; and
   in the evaluation step (f), an evaluation value is calculated based on the initial value data, the exposure data and the control data, and the toxicity of the test substance is evaluated based on the evaluation value.

4. The method according to claim 2, wherein
   in the exposure step (d), the algal cells after the confirmation step (c) is also mixed with a solvent for the test substance solution to prepare a control sample, and the control sample is cultured;
   in the measurement step (e), the delayed luminescence of the control sample is also measured as control data; and
   in the evaluation step (f), an evaluation value is calculated based on the initial value data, the exposure data and the control data, and the toxicity of the test substance is evaluated based on the evaluation value.

* * * * *